United States Patent
Vetter et al.

[11] Patent Number: 6,025,203
[45] Date of Patent: *Feb. 15, 2000

[54] DIAGNOSTIC TEST CARRIER AND METHODS IN WHICH IT IS USED TO DETERMINE AN ANALYTE

[75] Inventors: Peter Vetter, Schifferstadt; Helmut Leininger, Mannheim, both of Germany

[73] Assignee: Roche Diagnostics GmbH, Mannheim, Germany

[*] Notice: This patent is subject to a terminal disclaimer.

[21] Appl. No.: 08/897,608

[22] Filed: Jul. 21, 1997

[30] Foreign Application Priority Data

Jul. 23, 1996 [DE] Germany ............ 196 29 655

[51] Int. Cl.⁷ .................................................. G01N 33/48
[52] U.S. Cl. ................... 436/170; 436/177; 436/178; 422/56; 422/58
[58] Field of Search .................. 422/56, 57, 58, 422/61; 436/170, 177–178

[56] References Cited

U.S. PATENT DOCUMENTS

| | | |
|---|---|---|
| 4,542,739 | 9/1985 | Schäfer et al. . |
| 5,198,335 | 3/1993 | Sekikawa et al. ............ 422/56 |
| 5,284,622 | 2/1994 | Krause et al. . |
| 5,846,837 | 12/1998 | Thym et al. ................ 422/58 |

FOREIGN PATENT DOCUMENTS 0 388 782   9/1990   European Pat. Off. .

*Primary Examiner*—Lyle A. Alexander
*Attorney, Agent, or Firm*—Nikaido Marmelstein Murray & Oram, LLP.

[57] ABSTRACT

The invention concerns a diagnostic test carrier (1) containing a supporting layer (2) with a detection layer (3) arranged thereon containing the reagents required to determine an analyte in a liquid sample and a network (4) covering the detection layer (3) which is larger than the detection layer (3) and which is attached to the supporting layer (2), wherein the network (4) is a plied knitted fabric the threads of which are highly roughened on the side facing the detection layer (3) whereas the threads on the side of the knitted fabric which face away from the detection layer (3) are relatively smooth as well as the use of such a test carrier to determine an analyte in a liquid and the use of such a knitted fabric as a layer spreading liquid in a diagnostic test carrier. Moreover the invention concerns a method for the determination of an analyte in a liquid sample with the aid of a test carrier according to the invention.

30 Claims, 1 Drawing Sheet

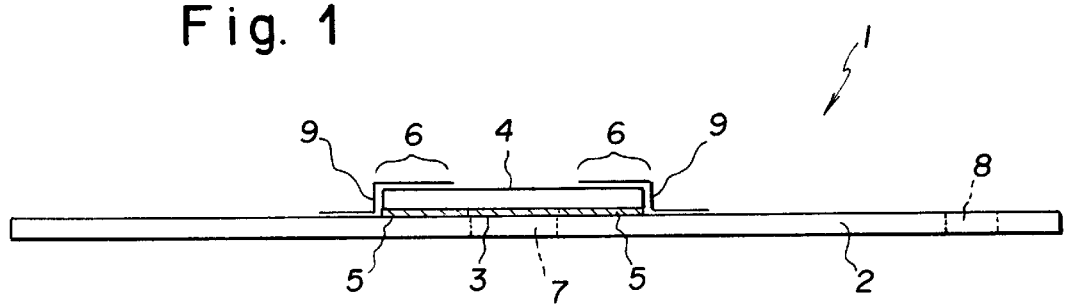
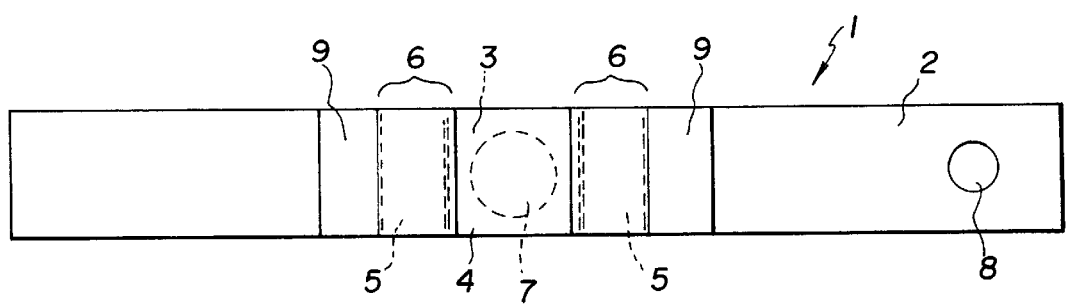

DIAGNOSTIC TEST CARRIER AND METHODS IN WHICH IT IS USED TO DETERMINE AN ANALYTE

The invention concerns a diagnostic test carrier containing a supporting layer with a detection layer arranged thereon containing reagents required to determine an analyte in a liquid sample and a network covering the detection layer which is larger than the detection layer and which is attached to the supporting layer. In addition the invention concerns the use of this diagnostic test carrier for the determination of an analyte in a liquid and the use of a knitted fabric that absorbs liquid as liquid spreading layers in a diagnostic test carrier.

So-called carrier-bound tests are often used for the qualitative or quantitative analytical determination of components of body fluids in particular of blood. In these the reagents are embedded in appropriate layers of a solid test carrier which is contacted with the sample. The reaction of the liquid sample and reagents leads to a detectable signal in particular to a change in colour which can be analyzed visually or with the aid of an instrument, usually by reflection photometry.

Test carriers are frequently in the form of test strips which are composed essentially of an elongated supporting layer made of plastic material and detection layers as test zones mounted thereon. However, test carriers are also known which are shaped as small quadrangular or rectangular plates.

Test carriers of the type referred to above are known for example from the German Patent document 21 18 455. In this document diagnostic test carriers for the detection of analytes in liquids are described which are composed of a supporting layer and at least one detection layer containing the detection reagents whose surface which does not rest against the supporting layer is provided with a covering layer. The covering layer can be composed of a fine-meshed network in the form of a fabric, knitted fabric or fleece. Plastic fabrics are stated as being preferred networks in order to achieve a rapid wetting of the detection layer with sample liquid and to avoid interfering chromatographic effects. In order to detect an analyte in a liquid such a diagnostic test carrier is immersed in an appropriate liquid. The detection layer thus comes into contact with a very large excess of liquid which cannot be taken up by the test carrier. However, different colour intensities are observed depending on the duration of contact of the detection layer with the liquid to be examined. As a rule longer contact times lead to more positive results. Hence a correct quantitative analyte determination is not possible in this manner.

The object of the present invention is to provide a diagnostic test carrier for the quantitative determination of an analyte in a liquid on which an undosed amount of sample liquid can be applied and with which an excess of sample liquid should not lead to time-dependent false positive results.

This object is achieved by the invention characterized in more detail in the patent claims.

The subject matter of the invention is namely a diagnostic test carrier with a supporting layer and a detection layer arranged thereon which contains the reagents required to determine an analyte in a liquid sample. The detection layer is covered by a network which is larger than the detection layer and which is fastened onto the supporting layer outside the detection layer. The network of the diagnostic test carrier according to the invention is a multi-thread knitted fabric the threads of which are strongly roughened on the side facing the detection layer whereas the threads on the side of the knitted fabric which faces away from the detection layer are smooth.

The invention in addition concerns the use of such a diagnostic test carrier to determine an analyte in a liquid. Hence a method for the determination of an analyte in a liquid sample with the aid of such a diagnostic test carrier is also a subject matter of the invention in which sufficient sample liquid is applied to the side of the network facing away from the detection layer to saturate the detection layer with liquid. The network then leads excess liquid from the detection layer into the region of the network which extends beyond the detection layer whereupon the detection layer can then be observed for a change in colour. The intensity of the colour change is a measure of the presence or the amount of analyte in the examined liquid sample.

Finally a subject matter of the invention is also the use of a sheet-like knitted fabric that absorbs liquid with a knitting thread made of a completely synthetic material and of hydrophilic threads made of absorptive yarns which are worked into the knitted fabric as weft threads which are roughened on one side of the knitted fabric as a liquid spreading layer in a diagnostic test carrier. Such a knitted fabric is known for example from the German Patent document 32 13 673 from a completely different technical field, namely as a wound textile with wound secretion absorptive properties which does not adhere to the wound. The features of the knitted fabric mentioned in this patent also apply to the network used according to the present invention. Thus this network is an elastic knitted fabric with a knitting thread composed of a first material and threads worked in composed of a very absorptive second material as weft threads. The second material is advantageously more hydrophilic than the first material. This can be achieved when the first material is composed above all of a fully synthetic material such as for example polyester, polyamide or polypropylene. In contrast the second material should be composed of highly absorptive yarns such as for example of cotton, viscose staple fiber or linen. The knitted fabrics that can be used according to the invention are characterized among others in that the knitting thread is located on the side of the knitted fabric that faces away from the detection layer and the well threads are on the side of the knitted fabric that faces towards the detection layer.

The German Patent document mentioned above, 32 13 673, is hereby incorporated by reference for the knitted fabric.

Surprisingly the knitted fabric known from the state of the art only as a wound textile is excellently suitable in a diagnostic test carrier for spreading liquid rapidly and uniformly and for conducting liquid away from an underlying layer if the network is larger than this underlying layer so that the excess liquid can be absorbed by the part of the network which extends beyond the underlying layer.

In a diagnostic test carrier according to the invention materials which come into particular consideration for the supporting layer are those which do not absorb the liquids to be examined. These are so-called non-absorptive materials, plastic foils made for example of polystyrene, polyvinyl chloride, polyester or polyamide being particularly preferred. However, it is also possible to impregnate absorptive materials such as wood, paper or cardboard with water-repellent agents or to coat them with a water-resistant film in which case silicones or hard fats can be used as hydrophobing agents and for example nitrocellulose or cellulose acetate can be used as film formers. Metal foils or glass are suitable as further supporting materials.

In contrast for a detection layer it is necessary to use materials which are able to take up the liquid to be examined together with the components contained therein. These are so-called absorptive materials such as fleeces, fabrics, knitted fabrics or porous plastic materials which can be used as layer materials. The materials which come into consideration for the detection layer must of course also be able to carry reagents that are necessary for the detection of the analyte to be determined. In the simplest case all reagents required for the analyte test are on one layer. However, cases are also conceivable for which it is more advantageous to divide the reagents among several absorptive material layers which are then arranged on top of one another with their whole faces in contact. The term "detection layer" used in the following is intended to encompass those cases in which the reagents are located either only in or on one layer or in two or even more layers arranged as described above.

In addition the detection layer can also contain a layer which is able to separate plasma or serum from whole blood such as for example a glass fiber fleece as is known for example from EP-B-0 045 476. One or several such separating layers can lie on top of one or several layers which carry detection reagents. Such a structure is also intended to be included by the term "detection layer".

Preferred materials for the detection layer are papers or porous plastic materials such as membranes. Asymmetric porous membranes are particularly preferred which are arranged advantageously such that the sample liquid to be examined is applied to the large-pored side of the membrane and the analyte is determined from the fine-pored side of the membrane. Polyamide, polyvinylidene difluoride, polyethersulfone or polysulfone membranes are quite especially preferred as porous membrane materials. Polyamide 66 membranes are in particular excellently suitable as the test carrier according to the invention. The reagents for the determination of the analyte to be detected are usually introduced by impregnation into the aforementioned materials.

However, so-called open films also come into consideration for the detection layer as described for example in EP-B-0 016 3 87. For this an aqueous dispersion of film-forming organic plastic solids are added as fine insoluble organic or inorganic particles and the reagents required for the detection reaction are additionally added. Suitable film formers are preferably organic plastics such as polyvinyl esters, polyvinyl acetates, polyacrylic esters, polymethacrylic acid, polyacrylamides, polyamides, polystyrene, mixed polymers such as of butadiene and styrene or of maleic acid esters and vinyl acetate or other film forming natural and synthetic organic polymers as well as mixtures of the same in the form of aqueous dispersions. The dispersions can be distributed onto a base to form a uniform layer which yields a water-resistant film after drying. The dry films have a thickness of 10 $\mu$m to 500 $\mu$m preferably of 30 to 200 $\mu$m. The film can be used with the base together as a carrier or can be applied to another carrier for the, detection reaction. Although the reagents required for the detection reaction are normally added to the dispersion used to produce the open films, it may also be advantageous to impregnate the film that is formed with the reagents after it has been manufactured. It is also possible to pre-impregnate the fillers with the reagents. Which reagents can be used to determine a particular analyte is known to a person skilled in the art. This does not need to be elucidated here in more detail.

In the diagnostic test carrier according to the invention the network which covers the detection layer is larger than the underlying detection layer. The part of the network which extends beyond the detection layer is fixed to the supporting layer. The attachment can be achieved by methods known to a person skilled in the area of test carrier technology. For example it can be attached by heat-sealing layers (polyethylene), hot-setting adhesive or hardening cold-setting adhesive. Double-sided adhesive strips have also proven advantageous. However, in all cases it is important that the attachment of the network to the supporting layer is such that a capillary active liquid transport is possible from the detection layer into that part of the network which is attached to the supporting layer. This capillary active liquid transport must in particular be possible when the detection layer is saturated with liquid.

In order to determine the analyte to be detected in the sample liquid, the detection layer is visible through the supporting layer in the diagnostic test carrier according to the invention. This can be achieved by a transparent supporting layer. However, it is also possible that the supporting layer has a hole which is covered by the detection layer. The detection layer is then visible through the hole. In a preferred embodiment of the diagnostic test carrier according to the invention there is a hole in the supporting layer below the detection layer through which the detection layer can be observed. The hole has a somewhat smaller diameter than the smallest linear dimension of the detection layer so that the detection layer outside the hole rests on the supporting layer and can be attached there. As a rule the detection layer is attached by a double-sided adhesive tape and the overlying network and its attachment are adequately attached to the supporting layer.

In order to carry out a method for the determination of analyte in a liquid sample with the aid of a diagnostic test carrier according to the invention sufficient sample liquid is applied to the side of the network which faces away from the detection layer to completely saturate the detection layer with liquid passing through the network. Body fluids such as blood, plasma, serum, urine, saliva etc. come into particular consideration as the sample liquid. Blood or liquids derived from blood such as plasma or serum as well as urine are particularly preferred sample liquids. Excess liquid is led away by the network from the detection layer into the region of the network which extends beyond the detection layer. Then a signal can be detected in the detection layer when the analyte to be determined is present. Such a signal is preferably a change in colour which is understood as colour formation, loss of colour as well as colour transition. The intensity of the colour change is a measure of the amount of analyte in the examined liquid sample. It can be evaluated visually or quantitatively with the aid of an instrument, usually by reflection photometry.

The regions of the network which extend beyond the detection layer can be advantageously covered to mark the sample fluid application site. For this purpose two water-impermeable inert layer materials can for example be attached to the network in such a way that the region of the network which lies over the hole in the supporting layer under the detection layer remains free for sample application. It has proven to be particularly advantageous when these layer materials are adhesive foils the adhesive side of which does not only contact the regions of the network which extend beyond the detection layer but are also additionally attached to the supporting layer. In addition to marking the sample liquid application site such a cover also supports the capillary forces which conduct excess liquid away from the detection layer. In addition the cover also has the effect that excess liquid that is led away from the detection layer is protected from contact and that such liquid cannot easily drip from the test carrier.

A major advantage of the diagnostic test carrier according to the invention is that it is not necessary to apply a predetermined volume of a sample liquid to the test carrier. It is only necessary to ensure that an excess is used so that the detection layer is completely saturated with liquid. As already mentioned excess liquid is conducted away from the detection layer by the network protruding beyond the detection layer. Since excess liquid is conducted away from the detection layer, hygienic aspects are also taken into consideration. A dripping of liquid from the test carrier or contact of liquid for example with parts of an instrument into which the test carrier is placed for instrumental evaluation is reliably avoided. This is a very important aspect in the examination of blood or samples derived from blood such as plasma or serum.

The size of the region of the network that extends beyond the detection layer depends on the largest sample volume expected in practice so that liquid that is really in excess can also be conducted away from the detection layer. In this manner the signal intensity which occurs when an analyte is present is independent of the amount and the duration of contact of the sample liquid with the detection layer. The colour which is formed after completion of the detection reaction, usually within a few seconds until a few minutes, thus remains unchanged for the measurement. It is merely determined by the stability of the colour generating system but not for example by analyte which diffuses back from the excess liquid into the detection layer. False positive results are also avoided and a quantitative analyte determination becomes possible.

BRIEF DESCRIPTION OF THE DRAWINGS

A preferred embodiment of the diagnostic test carrier according to the invention are shown in FIG. 1 and 2.

FIG. 1 shows a cross-section through a preferred diagnostic test carrier according to the invention.

FIG. 2 shows a top view of the diagnostic test carrier according to the invention shown in cross-section in FIG. 1.

The reference numerals used in the figures have the meanings.
1) diagnostic test carrier
2) supporting layer
3) detection layer
4) network
5) attachment layer
6) region of the network that extends beyond the detection layer
7) hole in the supporting layer under the detection layer
8) positioning hole
9) cover The cross-section through a diagnostic test carrier (1) according to the invention shown in FIG. 1 and the top view thereof shown in FIG. 2 show a supporting layer (2) with the detection layer (3) and the network (4) covering the detection layer (3) which is attached to the supporting layer (2) in the region (6) that extends beyond the detection layer (3) by means of an attachment layer (5). A hole (7) is located in the supporting layer (2) under the detection layer (3) through which the detection layer (3) is visible. The positioning hole (8) enables the test strip to be held at an exact predetermined position of the apparatus in the case of measurement by an apparatus such as by reflection photometry. This can for example be achieved by a pin which extends into the positioning hole (8) and thus holds the test strip (1) at a predetermined position. The cover foil (9) is attached to the supporting layer (2) and covers the region (6) of the network (4) which extends beyond the detection layer (3) so that the region of the network (4) which lies over the detection layer (3) remains free.

EXAMPLE 1

Production of a Diagnostic Test Carrier According to the Invention

A test carrier according to FIG. 1 is produced by the following working steps:

A 6 mm wide double-sided adhesive tape (polyester support and synthetic rubber adhesive) is applied to a polyester supporting layer containing titanium dioxide. This composite is jointly punched with a 6 mm distance between the holes in order to produce the measuring holes. Afterwards the protective paper of the double-sided adhesive is removed.

A detection zone composed of 2 film layers is produced as follows:

A. The following components ire added together in the following composition to a beaker as pure substances or in the form of stock solutions and admixed by stirring:

| | |
|---|---|
| Water: | 820.0 g |
| citric acid monohydrate: | 2.5 g |
| calcium chloride dihydrate | 0.5 g |
| sodium hydroxide: | 1.4 g |
| xanthan gum: | 3.4 g |
| tetraethylammonium chloride: | 2.0 g |
| N-octanoyl-N-methyl-glucamide: | 2.1 g |
| polyvinylpyrrolidone (MW 25000): | 3.5 g |
| Transpafill ® (sodium-aluminium silicate) | 62.1 g |
| polyvinylpropionate dispersion (50% by weight in water): | 60.8 g |
| bis-(2-hydroxyethyl)-(4-hydroximinocyclohexa-2,5-dienylidine)-ammonium chloride: | 1.2 g |
| 2,18-phosphoromolybdic acid hexasodium salt: | 16.1 g |
| pyrroloquinoline-quinone: | 32 mg |
| glucose dehydrogenase rec. from Acinetobacter 1.7 MU calcoaceticus, EC 1.1.99.17: | (2.4 g) |
| 1-hexanol: | 1.6 g |
| 1-methoxy-2-propanol: | 20.4 g |

The total composition is adjusted with NaOH to a pH of ca. 6 and then applied with an area weight of 89 g/qm onto a 125 μm thick polycarbonate foil and dried.

B. The following components are added together in the following composition to a beaker as pure substances or in the form of stock solutions and admixed by stirring:

| | |
|---|---|
| water: | 579.7 g |
| sodium hydroxide: | 3.4 g |
| Gantrez ® (methyl vinyl ether maleic acid-copolymer): | 13.8 g |
| N-octanoyl-N-methyl-glucamide: | 3.6 g |
| tetraethylammonium chloride: | 9.7 g |
| polyvinylpyrrolidone (MW 25000): | 20.2 g |
| titanium dioxide: | 177.1 g |
| kieselguhr: | 55.3 g |
| polyvinylpropionate dispersion (50% by weight in water): | 70.6 g |
| 2,18-phosphoromolybdic acid hexasodium salt: | 44.3 g |

-continued

| | |
|---|---|
| potassium hexacyanoferrate (III): | 0.3 g |
| 1-hexanol: | 1.6 g |
| 1-methoxy-2-propanol: | 20.4 g |

The total composition is adjusted with NaOH to a pH of ca. 6 and then applied with an area weight of 104 g/qm onto a polycarbonate foil coated as described in A. and dried.

A 5 mm wide strip of the detection layer produced in this manner is fitted exactly and glued onto the supporting layer with its foil side on the punched double-sided adhesive tape.

Double-sided adhesive tapes as spacers (PVC support and natural rubber adhesive) are glued onto the support foil on both sides and directly adjoining the detection layer. In the present example one spacer is 6 mm and the other is 9 mm wide. Subsequently the protective foil of the two double-sided adhesive tapes is removed.

A Doubleface 450 (Karl Otto Braun Company, Wolfstein, Germany) knitted fabric according to DE-C-32 13 673 impregnated with a wetting agent is placed as a network on this compound structure and glued by pressing.

Two single-sided adhesive tapes (PVC support and natural rubber adhesive) are glued onto the network as covers in such a way that the spacers are completely covered and that there is still at least a slight overlap with the reaction zone. This finishes the tape material.

The tape material is cut into 6 mm wide test carriers in such a way that the measuring hole is in the middle of the test carrier.

Uniform and reproducible colours that are stable over time and are proportional to the amount of glucose in the blood are always generated in the detection layer with different blood volumes (5, 8, 10 and 15 $\mu$l) using test carriers produced in this manner. The volume dependency is less than 2% with respect to a reflectance measurement value that is obtained with 10 $\mu$l sample.

What is claimed is:

1. A diagnostic test carrier for the determination of an analyte in a liquid sample, comprising
   a supporting layer;
   a detection layer arranged on the supporting layer, said detection layer having reagents incorporated therewith for the detection of an analyte in a liquid sample; and
   a network covering the detection layer, wherein the network is larger than the detection layer, the network extends beyond the detection layer, and the network is attached to the supporting layer, such that capillary liquid transport is possible from the detection layer to a part of the network which extends beyond the detection layer;
   wherein the network is a multi-thread knitted fabric having, a thread of a first material located on a side of the fabric facing away from the detection layer, and a thread of a second material located on a side of the fabric facing the detection layer, and wherein the thread of the second material has a surface roughness which is greater than a surface roughness of the thread of the first material.

2. The diagnostic test carrier according to claim 1, wherein the network is an elastic knitted fabric, wherein the thread made of the first material is a knitting thread, wherein the second material is more hydrophilic than the first material, and wherein the threads of the second material are worked into the fabric as weft threads.

3. The diagnostic test carrier according to claim 2, wherein the weft threads are comprised of absorptive yarns which are substantially roughened on the side of the knitted fabric which faces the detection layer.

4. The diagnostic test carrier according to claim 2, wherein the knitting thread is comprised of synthetic material.

5. The diagnostic test carrier according to claim 1, wherein the supporting layer does not substantially absorb the liquid sample to be determined.

6. The diagnostic test carrier according to claim 5, wherein the supporting layer is a plastic foil.

7. The diagnostic test carrier according to claim 5, wherein the supporting layer is an absorptive material coated with at water-resistant film.

8. The diagnostic test carrier according to claim 1, wherein the detection layer is a material which can absorb the liquid sample to be determined.

9. The diagnostic test carrier according to claim 1, wherein the detection layer is an assymmetric porous membrane having a large pore side to which the liquid sample is applied, and a small pore side.

10. The diagnostic test carrier according to claim 9, wherein the detection layer is polyamide 66.

11. The diagnostic test carrier according to claim 1, wherein the detection layer has at least two material layers.

12. The diagnostic test carrier according to claim 11, wherein the reagents are present in at least one material layer of the detection layer.

13. The diagnostic test carrier according to claim 1, wherein the liquid sample is a body fluid.

14. The diagnostic test carrier according to claim 13, wherein the liquid sample is whole blood.

15. The diagnostic test carrier according to claim 1, wherein the detection layer further comprises a layer which can separate plasma or serum from the whole blood, and which is positioned on top of at least one material layer having reagents incorporated therewith.

16. The diagnostic test carrier according to claim 15, wherein the layer which can separate plasma or serum from the whole blood is a glass fiber fleece.

17. The diagnostic test carrier according to claim 1, wherein the detection layer has two sides and is visible from at least one side.

18. The diagnostic test carrier according to claim 17, wherein the supporting layer is substantially transparent to permit the detection layer to be visible therethrough.

19. The diagnostic test carrier according to claim 17, wherein the supporting layer has at least one hole, through which the detection layer is visible, and wherein the hole is smaller than the detection layer such that the detection layer contacts at least a portion of an area of the supporting layer surrounding the hole.

20. The diagnostic test carrier according to claim 1, wherein a cover is located over the region of the network which extends beyond the detection layer, and wherein the cover is arranged such that the region of the network which lies over the detection layer is not covered by the cover.

21. The diagnostic test carrier according to claim 20, wherein the cover is attached to the supporting layer.

22. The diagnostic test carrier according to claim 1, wherein the detection layer carries the reagents thereon.

23. The diagnostic test carrier according to claim 1, wherein the detection layer has the reagents embedded therein.

24. A method of determining an analyte in a liquid sample, using a diagnostic test carrier comprising a supporting layer, a detection layer arranged on the supporting layer, said detection layer having reagents incorporated therewith for the detection of an analyte in a liquid sample, and a network covering the detection layer, wherein the network is a multi-thread knitted fabric having a thread of a first material located on a side of the fabric facing away from the detection layer, and a thread of a second material located on a side of the fabric facing the detection layer, wherein the thread of the second material has a surface roughness which is greater than a surface roughness of the thread of the first material, wherein the network is larger than the detection layer, the network extends beyond the detection layer, and the network is attached to the supporting layer such that capillary liquid transport is possible from the detection layer to a part of the network which extends beyond the detection layer, comprising passing the liquid sample through the network to the detection layer, in a sufficient amount as to saturate the detection layer with liquid sample, with removal of excess liquid through capillary action into the region of the network which extends beyond the detection layer, to produce a detectable signal in the detection layer from reaction of the liquid sample with the reagents in the detection layer; and detecting the signal.

25. The method of determining an analyte in a liquid sample according to claim 24, wherein the detectable signal is a color change signal.

26. The method of determining an analyte in a liquid sample according to claim 24, wherein the liquid sample is a body fluid.

27. The method of determining an analyte in a liquid sample according to claim 24, wherein the liquid sample is whole blood.

28. The diagnostic test carrier according to claim 24, wherein the detection layer carries the reagents thereon.

29. The diagnostic test carrier according to claim 24, wherein the detection layer has the reagents embedded therein.

30. A diagnostic test carrier for the determination of an analyte in a liquid sample, comprising a supporting layer;

a detection layer means, arranged on the supporting layer, for determining an analyte in a liquid sample; and a network means, covering the detection layer means, for allowing transport of the liquid sample therethrough from the exterior of the test carrier to the detection layer means, and for removing excess liquid from the detection layer means by capillary action.

* * * * *